United States Patent

Raab et al.

(10) Patent No.: US 6,376,696 B1
(45) Date of Patent: Apr. 23, 2002

(54) ANTIMICROBIAL SILOXANE QUAT FORMULATIONS AND THEIR PREPARATION AND USE

(75) Inventors: Klaus Raab, Burgkirchen (DE); Walter Bender, Kirchberg (CH)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/596,419

(22) Filed: Jun. 19, 2000

(30) Foreign Application Priority Data

Jun. 19, 1999 (DE) .......................... 199 28 127

(51) Int. Cl.$^7$ .................................. C07F 7/10
(52) U.S. Cl. ......................... 556/423; 514/63
(58) Field of Search ............... 556/423; 514/63

(56) References Cited

U.S. PATENT DOCUMENTS

| | | | |
|---|---|---|---|
| 4,005,119 A | * | 1/1977 | Heckert et al. ............... 556/423 |
| 4,845,256 A | | 7/1989 | Mebes et al. |
| 4,883,917 A | | 11/1989 | Smith et al. |

FOREIGN PATENT DOCUMENTS

| | | |
|---|---|---|
| EP | 0 108 853 | 5/1984 |
| EP | 0 415 540 | 3/1991 |
| WO | WO 87/06587 | 11/1987 |
| WO | WO 99/03866 | 1/1999 |

OTHER PUBLICATIONS

PCT Search Report.
K.J. Huttinger, Chemiker–Zeitung, 111, 1987, p. 213–220.

* cited by examiner

Primary Examiner—Paul F. Shaver

(74) Attorney, Agent, or Firm—Richard P. Silverman

(57) ABSTRACT

Disclosed is a process for preparing an antimicrobial formulation by reacting a compound of the formula 1

$$(R^1O)_3Si-(CH_2)_3-X \quad (1)$$

with a compound of the formula 2

$$(H_3C)NR^2R^3 \quad (2)$$

where
$R^1$ is $C_1$–$C_4$-alkyl
$R^2$ is $C_8$–$C_{20}$-alkyl
$R^3$ is methyl or $C_8$–$C_{20}$-alkyl
X is Cl or Br,
excluding iodides, in a molar ratio of (1):(2)=1:0.9 to 1:1.4, which comprises conducting said reaction in a solvent conforming to the formula 3

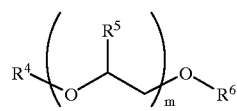

(3)

where
$R^4$ is $C_1$–$C_4$-alkyl
$R^5$ is H or methyl
$R^6$ is H or methyl
m is 2, 3, 4 or 5,
subject to the proviso that when m is 2 $R^4$ and $R^6$ are not both methyl, and not removing this solvent after said reaction, or adding this solvent after said reaction.

Further disclosed is an antimicrobial formulation obtainable by the process described above.

11 Claims, No Drawings

ANTIMICROBIAL SILOXANE QUAT FORMULATIONS AND THEIR PREPARATION AND USE

BACKGROUND OF THE INVENTION

The present invention relates to formulations comprising quaternary ammonium compounds substituted by a trialkoxysilane group, hereinafter called siloxane quats for short, and special solvents and also to the preparation and use of these siloxane quat formulations.

There is extensive patent literature relating to the preparation of quaternary ammonium compounds having a trialkoxysilane substituent and one or two fatty alkyl radicals and to the use of these compounds as biocides. The trialkoxysilane substituent augments the tendency of quaternary ammonium compounds to form permanent finishes on surfaces of various kinds, for example textiles composed of polyamide, cotton or polyester, wood, paper, glass, plastics or metals. The surfaces finished with these compounds acquire durable water-resistant antimicrobial protection as a result. For instance, a solution of 3-(trimethoxysilyl) propyloctadecyl-dimethylammonium chloride in methanol is commercially available for the antimicrobial finishing of various surfaces.

EP-A-0 108 853 describes the preparation of 3-(trimethoxysilyl)propyl-didecylmethylammonium chloride from 3-chloropropyltrimethoxysilane and didecylmethylamine without solvent or in a solvent such as methanol. Without further details being provided, solvents useful for bactericidal or fungicidal applications are said to be water, water-miscible solvents such as alcohols, for example methanol, ethanol and butanol, methylcellosolve, ethylcellosolve and ketones such as methyl ethyl ketone. For textile treatment, solvents such as hydrocarbons, chlorinated hydrocarbons, ethers and benzene are said to be alternatively useful.

WO-87/06587 discloses preparing compounds of the type

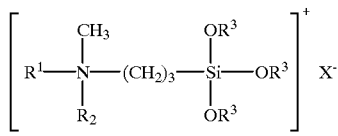

by reacting tertiary amines with 3-chloropropyltrialkoxysilanes under alkali metal iodide catalysis. The solvent for this catalytic reaction is selected from certain glycol ethers.

Further quaternary ammonium compounds, including some substituted by trialkoxysilane radicals, are recited in U.S. Pat. No. 4,883,917. They are prepared at 50–100° C. either without solvent or in the solvents used in many examples, ethyl acetate, methyl ethyl ketone and para-dioxane. Further possible solvents for quaternization reactions are said to be tetrahydrofuran, dimethoxyethane and diglyme.

EP-A-0 415 540 describes using quaternary ammonium compounds substituted by trialkoxysilane radicals for the antibacterial and fungicidal finishing of textile fabrics to eliminate odor. The preferred compound is 3-(trimethoxysilyl) propyloctadecyl-dimethylammonium chloride. A method for preparing these compounds is not disclosed, although there is a reference to the prior art.

K. J. Hüttinger, Chemiker-Zeitung, 111 (1987) pages 213–220 describes the use of quaternary trialkoxysilane for preparing carrier-bound agents for disinfecting water. With this technique, unlike chlorination or ozonization, say, no active compound passes into the water. The quaternary trialkoxysilanes are synthesized in methanol or ethylene glycol monomethyl ether at 110° C. in an autoclave.

The solvents which in the above-described prior art are used during the reaction of haloalkyltrialkoxysilanes with tertiary amines or are mixed in after the reaction have the drawback—which weighs heavily in the textile industry in particular—of having low flash points and being highly flammable. Many of the solvents hitherto used, for example methanol, have a boiling point below the reaction temperatures, so that their use requires that the reaction be carried out under elevated pressure, and this naturally requires increased expenditure on apparatus and safety. Quaternary ammonium compounds having trialkoxysilane substituents are usually solids, depending on the alkyl chain length. Since solids are more costly to handle and meter than liquids, most users prefer liquid formulations.

SUMMARY OF THE INVENTION

It is an object of the present invention to develop liquid siloxane quat formulations that do not have the disadvantage of having a low flash point and being highly flammable. The solvents used shall be compatible with the siloxane quats, shall augment the end use and shall have favorable ecotoxicological properties. It is desirable, but not absolutely necessary, for them also to be useful as solvents during the reaction of haloalkyltrialkoxysilanes with tertiary amines. It is a further object to develop a siloxane quat formulation which, even at low concentration, is superior to the prior art with regard to activity against microorganisms such as bacteria and fungi on textile surfaces in particular.

These objects are achieved by the process of the invention for preparing the siloxane quat formulations of the invention using specific glycol ethers or specific dialkylglycols as solvents.

DESCRIPTION OF THE PREFERRED EMBODIMENTS

The invention accordingly provides a process for preparing an antimicrobial formulation by reacting a compound of the formula 1

$$(R^1O)_3Si—(CH_2)_3—X \qquad (1)$$

with a compound of the formula 2

$$(H_3C)NR^2R^3 \qquad (2)$$

where $R^1$ is $C_1$–$C_4$-alkyl $R^2$ is $C_8$–$C_{20}$-alkyl $R^3$ is methyl or $C_8$–$C_{20}$-alkyl X is Cl or Br, excluding iodides, in a molar ratio of (1):(2)=1:0.9 to 1:1.4, which comprises conducting said reaction in a solvent conforming to the formula 3

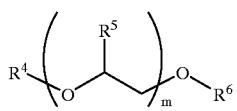

(3)

where
R$^4$ is C$_1$–C$_4$-alkyl
R$^5$ is H or methyl
R$^6$ is H or methyl
m is 2, 3, 4 or 5, subject to the proviso that when m is 2 R$^4$ and R$^6$ are not both methyl, and not removing this solvent after said reaction, or adding this solvent after said reaction.

The invention further provides an antimicrobial formulation obtainable by the process described above.

In a preferred embodiment of the invention, R$^1$ is methyl. X is preferably chlorine.

In a further preferred embodiment, R$^2$ is C$_{10}$–C$_{18}$-alkyl, especially C$_{12}$–C$_{16}$-alkyl, specifically a mixture of C$_{12}$-, C$_{14}$- and C$_{16}$-alkyl radicals.

In a further preferred embodiment, R$^3$ is C$_8$–C$_{16}$-alkyl or methyl. R$^3$ is particularly preferably methyl when R$^2$ is C$_{12}$–C$_{18}$-alkyl, especially when R$^2$ is C$_{14}$-alkyl.

In a further preferred embodiment, R$^4$ is methyl. R$^5$ is preferably hydrogen. R$^6$ is preferably hydrogen. m is preferably 3 or 4.

The process of the invention is preferably carried out at temperatures of 100 to 140° C. Temperatures of 110 to 130° C. are particularly preferred.

The process is preferably carried out under a dry protective gas in the absence of water. The water content of the solvents should preferably be below 0.1%. Highly suitable solvents are dipropylene glycol monomethyl ether, tripropylene glycol monomethyl ether, dimethyltetraglycol, dimethylpolyglycbl having an average molar mass of about 200–350 g/mol. Particularly highly suitable are butyldiglycol, methylpolyglycol having an average molar mass of about 200–350 g/mol, and especially methyltriglycol and/or methyltetraglycol. These solvents are compatible with siloxane quats, augment the end use as antimicrobial formulations, possess favorable ecotoxicological properties and do not have the disadvantage of low flash point and high flammability. The reaction of haloalkyltrialkoxysilane with tertiary amine can be carried out in the presence of the abovementioned solvents, but it is preferable to conduct the reaction in the absence of these solvents and to add them only after the reaction has taken place, at a temperature at which the products of the reaction are still liquid. When siloxane quat formulations are prepared in the presence of solvents, small amounts of alcohol may be eliminated from the alkoxy group of the haloalkyltrialkoxysilane. These small amounts of alcohol can, if desired, be removed, for example by distillation or stripping under reduced pressure.

A particularly preferred siloxane quat formulation is prepared by reacting 3-chloropropyltrimethoxysilane and tetradecyldimethylamine in a molar ratio of 1:1 to 1:1.1 at 120° C. (±10° C.) without solvent and adding methyltriglycol after the reaction has taken place.

The formulation of the invention includes at least one siloxane compound ("siloxane quat"), which is preparable by reacting the compounds of the formulae 1 and 2, and a substance as per the formula 3. In a preferred embodiment, the fractions of siloxane quat and of substance of the formula 3 are 20:80 to 80:20% by weight, based on the weight of the formulation. Particular preference is given to fractions of 40:60 to 60:40, especially 45:55 to 55:45, % by weight.

The process of the invention provides compounds of the formula 4

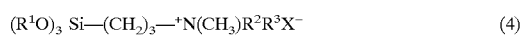

(4)

where R$^1$, R$^2$, R$^3$ and X are each as defined above.

In addition, the process of the invention provides compounds of the formula 5

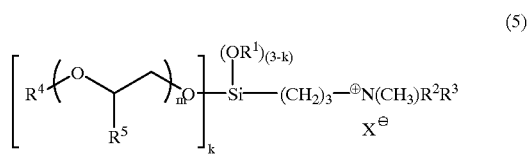

(5)

where k is 1, 2 or 3 and the remaining substituents are each as defined above.

These compounds constitute a further part of the subject-matter of the invention.

The formulations of the invention are useful for conferring an antimicrobial finish on surfaces. These surfaces can be, for example, textile fabrics, glass, wood, cellulose, metals or plastics. When used for finishing textiles, the formulation of the invention is preferably dissolved in water at a concentration of 5 to 100 g/l and applied in that form to the textiles. The amount of formulation remaining on the textiles is generally 0.2 to 3%, preferably 0.5 to 1%, by weight, based on the dry fabric weight.

The formulation of the invention can be applied by padding, exhaustion techniques at bath temperatures of 20 to 70° C., foaming or spraying. For spray application, the preferred concentration of the aqueous solution of the formulation according to the invention is 10 to 300 g/l.

The formulation of the invention can be used in the form of an aqueous solution for the antimicrobial finishing of fibers, yarns or fabrics composed of cotton or nylon or polyester or wool or mixtures thereof or of these fiber varieties with polyolefin fibers, preferably polypropylene, by the padding process, by the exhaustion process, by spraying processes or by foaming and application of the foam.

The formulation of the invention can also be used together with other textile chemicals, such as pure or mixed carboxylic acid hand modifiers, such as lactic acid and tartaric acid, such as wax, stearate or silicone sewing thread lubricants, such as silicone or paraffin hydrophobicizers, fluorocarbons with or without melamine derivative extenders, resins such as melamine resins, urea-formaldehyde resins, phenolic resins or polyester resins alone or in combination.

The above-described formulations likewise provide good results on being dissolved in water in concentrations within the range of 5 g/l to 100 g/l and being foamed up with a foaming agent such as an alkanesulfonate, an alkylamine oxide, an alkyl sulfate, an alkyl ether sulfate and salts thereof, preferably an alkyl sulfate, and on applying the foam, which as well as the foaming agent includes the formulation alone or in combination with other textile chemicals, to textiles.

Above-described formulations can be successfully used with good results in combinations with other textile chemicals by using them as solutions, preferably as aqueous solutions, together with other textile chemicals such as hand modifiers, sewing thread lubricants, hydrophobicizers, fluorocarbons with or without extenders, resins to modify the wet crease properties, the anti-slip and anti-laddering finish, permanent hand, stiffening and filling effects and flame retardants, alone or in combination.

Embodiments of the invention will now be more particularly described by way of example.

EXAMPLES

Example 1

500 g of 3-chloropropyltrimethoxysilane and 620 g of tetradecyldimethylamine are initially charged to a 2 liter round-bottom flask equipped with internal thermometer, KPG stirrer, condenser and pressure maintenance valve under a nitrogen protective gas atmosphere and in the absence of atmospheric humidity. The clear reaction mixture is stirred at 120° C. for 48 hours. The yellow reaction product is cooled down and while still in the hot liquid state (about 50° C.) is mixed with stirring into 1120 g of methyltriglycol having a water content of less than 0.1%. The yield of siloxane quat formulation with 50% solvent is quantitative. Even after just 24 hours reaction time, while conversion is still incomplete, a very highly antimicrobially active siloxane quat formulation is obtained.

Example 2

119 g of 3-chloropropyltrimethoxysilane and 160 g of tetradecyldimethylamine are initially charged to a 1 liter round-bottom flask equipped with internal thermometer, magnetic stirrer, condenser and pressure maintenance valve under a nitrogen protective gas atmosphere and in the absence of atmospheric humidity. The clear reaction mixture is stirred at 140° C. for 24 hours. After cooling down to 80° C., 420 g of methyltetraglycol having a water content of less than 0.1% are metered into the yellowish orange reaction product with stirring. The yield of siloxane quat formulation with 60% solvent is quantitative.

Even after just 8 hours reaction time, while conversion is still incomplete, a very highly antimicrobially active siloxane quat formulation is obtained.

Example 3

119 g of 3-chloropropyltrimethoxysilane and 135 g of Genamin® LA 302 D, a mixture of various alkyldimethylamines having an average molar mass of about 225 g/mol (alkyl is mainly dodecyl and tetradecyl), are initially charged to a 500 ml round-bottom flask equipped with internal thermometer, magnetic stirrer, condenser and pressure maintenance valve under a nitrogen protective gas atmosphere and in the absence of atmospheric moisture. The clear reaction mixture is stirred at 140° C. for 16 hours. After cooling down, the still warm, liquid, yellowish orange reaction product is stirred into 170 g of methyltriglycol having a water content of less than 0.1%. The yield of siloxane quat formulation with 40% solvent is quantitative.

Example 4

50.0 g of 3-chloropropyltrimethoxysilane, 56.8 g of Genamin® LA 302 D (see Example 3) and 107 g of methyltriglycol having a water content of less than 0.1% are stirred at 120° C. in a 500 ml round-bottom flask equipped with internal thermometer, magnetic stirrer, condenser and pressure maintenance valve under a nitrogen protective gas atmosphere and in the absence of atmospheric humidity for a total of 23 hours. After cooling down to 80° C., small amounts of methanol which have formed during the reaction are distilled off for 3 hours at 30 mbar under reduced pressure and at 80° C. in a rotary evaporator. The yield of siloxane quat formulation with 50% solvent is almost quantitative.

Example 5

1000 g of 3-chloropropyltrimethoxysilane, 1472 g of Genamin® SH 302 D, a mixture of various alkyldimethylamines having an average molar mass of about 292 g/mol (alkyl is mainly octadecyl and hexadecyl), are initially charged to a 4 liter round-bottom flask equipped with internal thermometer, KPG stirrer, condenser and pressure maintenance valve under a nitrogen protective gas atmosphere and in the absence of atmospheric humidity. The clear reaction mixture is stirred at 100° C. for 168 hours. The reaction product, which is reddish in thick layers and yellow in thin layers, is cooled down and while still in the hot liquid state (about 60° C.) mixed with stirring into 2470 g of dipropylene glycol monomethyl ether. The yield of siloxane quat formulation with 50% solvent is quantitative.

Example 6

990.8 grams of tap water are initially charged and admixed with 0.2 gram of Sandozin® NRW, a wetting agent. To this solution are added 9.0 grams of a siloxane quat according to Example 1 of the invention in the form of a 50% solution in triethylene glycol monomethyl ether. The resulting solution is initially charged to the basin of a pad mangle, and a woven cloth of nylon-6,6 having a basis weight of 120 grams per square meter is pulled through this solution and squeezed off between the bowls in such a way that the cloth retains a liquid fraction of 58.4%, which corresponds to a pickup of 0.52% of the formulation according to the invention, based on the dry fabric weight. The cloth is dried in a tenter at 110° C. for two minutes. A sample of this cloth is tested for its effect on bacteria as described hereinafter. The durability of the antimicrobial finish to washing is determined by washing the cloth at 40° C. in a 30:1 ratio of wash liquor to fabric. The wash liquor contains 0.54 gram per liter of polyethoxylated nonylphenol having nine to ten ethylene oxide units per nonylphenol, namely Imbentin® N/52 from Kolb AG, Hedingen, Switzerland. The washing time is five minutes. The wash liquor is spun off in a spin-dryer, and the fabric is then rinsed under running cold water for around two minutes, spin-dried once more, the rinsing and the spin-drying are repeated once more, and the fabric is then dried at 80° C. Samples are tested in the agar diffusion test of Swiss standard SN 195 920 in the original state, after one wash and after three, five, ten and twelve washes. This test is carried out against the microorganisms of the ATCC 6538 strain of *Staphylococcus aureus*, against the ATCC 15442 strain of *Pseudomonas aeruginosa*, against the ATCC 11229 strain of *Escherichia coli* and against the ATCC 4352 strain of *Klebsiella pneumoniae*. An agar diffusion test was carried out according to Swiss standard SN 195 921 against the ATCC 10231 strain of *Candida albicans*. The samples all exhibited good activity against all the recited test microorganisms, not only in the original state but also after the washes, evaluated according to the cited standards. This means no colonization of the agar by the test organisms underneath the test samples, or the formation of a distinct zone of inhibition around the sample.

Example 7

15.0 grams of silicon quat as per Example 1, dissolved in 50% triethylene glycol monomethyl ether, are dissolved in 984.8 grams of water, admixed with 0.2 gram of Sandozin NRW, and applied by means of a pad mangle to a woven cotton fabric having a basis weight of around 196 grams per square meter in such a way as to obtain a pickup of 70%. The wet fabric is tenter dried at 110° C. and in the original state and after washing up to twelve times by the "Kokin-Boshu kako" method then tested in the agar diffusion test of the standard SN 195 920 or 195 921 against the microorganisms of the ATCC 6538 strain of *Staphylococcus aureus*, against the ATCC 15442 strain of *Pseudomonas aeruginosa*, against the ATCC 11229 strain of *Escherichia coli*, against the ATCC 4352 strain of *Klebsiella pneumoniae* and against the ATCC 10231 strain of *Candida albicans*. Virtually all results exhibit a good effect against the test microorganisms when evaluated according to the standards mentioned. A slight weakness in effect can only be observed against the ATCC 11229 strain of *Escherichia coli* after more than five wash cycles. But even here distinct inhibition of the bacterial growth is evident compared with an untreated piece of cotton material.

These results are surprisingly distinctly better in part than the results of Requat (brandname of Sanitized Inc.), a commercially available product containing 42% of didecylmethyl-3-(trimethoxysilyl)propylammonium chloride dissolved in methanol as silicon-functional quaternary ammonium compound.

Example 8

A polyester fabric having a basis weight of about 100 grams per square meter is padded by the method described in Example 6 with an aqueous solution containing 0.2 gram per liter of Sandozin NRW and 7 grams per liter of the 50% silicon quat solution of Example 1 in triethylene glycol monomethyl ether in such a way that a pickup of 75.2% is obtained. These samples are tested, not only in the original state but also after washes carried out according to Example 6, against the microorganisms specified in Example 6 according to the Swiss standards SN 195 920 or 195 921. All the test results obtained exhibited a good antimicrobial effect against all the test microorganisms enumerated in Example 6.

Example 9

A wool fabric having a basis weight of about 160 grams per square meter is padded by the method described in Example 6 with an aqueous solution containing 0.2 gram per liter of Sandozin NRW and 7 grams per liter of the 50% silicon quat solution of Example 1 in triethylene glycol monomethyl ether in such a way that a pickup of 75.2% is obtained. These samples are tested, not only in the original state but also after washes carried out according to Example 6, against the microorganisms specified in Example 6 according to the Swiss standards SN 195 920 or 195 921. All the test results obtained exhibited a good antimicrobial effect against all the test microorganisms enumerated in Example 6.

Example 10

35.5 grams of a cotton fabric are treated for 20 minutes at 40° C. in 706 milliliters of an aqueous liquor containing 0.18 gram in triethylene glycol monomethyl ether of the siloxane quat solution of Example 1 according to the invention. The liquor is subsequently spun off and the fabric dried at 80° C. These samples are tested, not only in the original state but also after washes carried out according to Example 6, against the microorganisms specified in Example 6 according to the Swiss standards SN 195 920 or 195 921. All the test results obtained exhibited a good antimicrobial effect against all the test microorganisms enumerated in Example 6. This example is repeated on fabrics composed of nylon, polyester and wool which are each finished with 0.5% of the formulation according to the invention and tested against the microorganisms mentioned according to SN 195 920 and SN 195 921 in the original state and after washes. All the samples achieved good antimicrobial results.

Example 11

A liter of aqueous liquor containing 7.5 grams of the formulation of Example 1 according to the invention, 40.0 grams of Nuva® CSF, a fluorocarbon of the perfluoroalkylacryloyl copolymer type from Clariant, 0.2 gram of Sandozin NRW, a rapid wetter from Clariant, is made up. This liquor is padded onto a cotton fabric and a nylon fabric in such a way that the formulation according to the invention is applied in an amount of 0.52% and the fluorocarbon in an amount of 2.77% in the case of the cotton fabric and 2.46% in the case of the nylon fabric. The fabrics are subsequently tenter dried at 110° C. for 2 minutes in each case and cured at 140° C. for 5 minutes. These fabrics are subsequently tested in the spray test according to AATCC 22. The cotton fabric thus finished achieves a value of 90, a minimally inferior value compared with the fabric treated with the fluorocarbon only. The nylon fabric achieves a value of 100 in the same test, which corresponds to the value of the fabric finished only with the fluorocarbon. In the oleo test of AATCC 118, both fabrics achieve the very good rating of 6 not only with just the fluorocarbon but also with the fluorocarbon together with the formulation according to the invention. The agar diffusion test of SN 195 920 gives excellent values with a distinct zone of inhibition against the bacterial strains of *Staphylococcus aureus* ATCC 6538 and *Klebsiella pneumoniae* ATCC 4352 and distinct inhibition of growth against the ATCC 11229 strain of *Escherichia coli*, namely a colonization of less than 5% of the sample area.

Example 12

A liter of aqueous liquor containing 7.5 grams of the formulation of Example 1 according to the invention, 30.0 grams of Sandolub® NV, a solubility improver from Clariant based on aliphatic hydrocarbons dispersed in water, 0.5 gram of Sandozin NRW, a rapid wetter from Clariant, is made up. This liquor is padded onto a cotton fabric and a nylon fabric in such a way that the amounts applied to the fabrics are 0.52% in the case of the formulation according to the invention and 2.0% in the case of the solubility improver. The fabrics are subsequently tenter dried at 110° C. for two minutes. The test for the antimicrobial values according to SN 195 920 produced excellent values against all bacteria mentioned in Example 6, varying between no colonization and distinct zones of inhibition measuring a number of millimeters.

Example 13

A liter of aqueous liquor containing 7.5 grams of the formulation of Example 1 according to the invention, 30.0 grams of Sandoperm® MEW, a modified polysiloxane, a softener from Clariant, 0.5 gram of Sandozin NRW, a rapid wetter from Clariant, is made up. This liquor is padded onto a cotton fabric and a nylon fabric in such a way that the amounts applied to the fabrics are 0.52% in the case of the formulation according to the invention and 2.0% in the case of the softener. The fabrics are subsequently tenter dried at 130° C. for two minutes. The test for the antimicrobial values according to SN 195 920 produced excellent values against all bacteria mentioned in Example 6, varying between no colonization and distinct zones of inhibition measuring a number of millimeters.

Example 14

A liter of aqueous liquor containing 7.5 grams of the formulation of Example 1 according to the invention, 200.0 grams of Pekoflam® OP, a flame retardant from Clariant based on an organic salt, 0.5 gram of Sandozin NRW, a rapid wetter from Clariant, is made up. This liquor is padded onto cotton fabric and a nylon fabric in such a way that the amounts applied to the fabrics are 0.5% in the case of the formulation according to the invention and 13.5% in the case of the flame retardant. The fabrics are subsequently tenter dried at 120° C. for two minutes. The test for the antimicrobial values according to SN 195 920 produced excellent values against all bacteria mentioned in Example 6, varying between no colonization and distinct zones of inhibition measuring a number of millimeters.

Example 15

A liter of aqueous liquor containing 7.5 grams of the formulation of Example 1 according to the invention, 40.0 grams of Appretan® EM, a polyvinyl acetate which is used as stiffening finish, 0.5 gram of Sandozin NRW, a rapid wetter from Clariant, is padded onto cotton fabric and a nylon fabric in such a way that the amounts applied to the fabrics are 0.5% in the case of the formulation according to the invention and 2.5% in the case of the finisher. The fabrics are subsequently tenter dried at 110° C. for two minutes. The test for the antimicrobial values according to SN 195 920 produced excellent values against all bacteria mentioned in Example 6, varying between no colonization and distinct zones of inhibition measuring a number of millimeters.

Example 16

To 480 milliliters of water are added 0.05 gram of the formulation of Example 1 according to the invention and 4.8 grams of a filter paper. The paper is left in the liquor for 20 minutes at 25° C. to 30° C. and it is subsequently dried at 80° C. The test for the antimicrobial values according to SN 195 920 produced excellent values against all bacteria mentioned in Example 6, varying between no colonization and distinct zones of inhibition measuring a number of millimeters.

Tables with the antimicrobial results from the examples:

In the results recited hereinbelow, numerals indicate the zones of inhibition in millimeters achieved in the agar diffusion test. These zones of inhibition are not necessarily identically reproducible in the same test, since the systems under investigation are biological systems with very many parameters. The statement is to be interpreted in such a way that the numerals 0 and greater mean that the sample itself is free of any colonization with the microorganisms mentioned and thus in the form tested is completely protected against infestation and colonization by the corresponding microorganism. The letter s indicates that the corresponding sample exhibited slight colonization with the corresponding microorganism of up to 5% of the sample area in the test. This means in practice a distinct inhibition of growth, and m means that the sample exhibited moderate colonization amounting to more than 5% to 40% of the area. This value is inadequate for antimicrobial protection.

Results to Example 6 (pad-mangle application to nylon):

| Microorganism | Original | 1 wash | 3 washes | 5 washes | 10 washes | 12 washes |
| --- | --- | --- | --- | --- | --- | --- |
| Staphylococcus aureus | 5 | 3 | 2 | 1 | 0 | 0 |
| Pseudomonas aeruginosa | 0 | 0 | 0 | 0 | 0 | 0 |
| Escherichia coli | 0 | 0 | 0 | 0 | 0 | 0 |
| Klebsiella pneumoniae | 2 | 0 | 0 | 0 | 0 | 0 |
| Candida albicans | 8 | 4 | 4 | 3 | 0 | 0 |

Results to Example 7 (pad-mangle application to cotton):

| Microorganism | Original | 1 wash | 3 washes | 5 washes | 10 washes | 12 washes |
| --- | --- | --- | --- | --- | --- | --- |
| Staphylococcus aureus | 6 | 5 | 3 | 2 | 2 | 1 |
| Pseudomonas aeruginosa | 0 | 0 | 0 | 0 | 0 | 0 |
| Escherichia coli | 0 | 0 | 0 | 0 | s | s |
| Klebsiella pneumoniae | 0 | 0 | 0 | 0 | 0 | 0 |
| Candida albicans | 0 | 0 | 0 | 0 | 0 | 0 |

Same finish and tests with Requat:

| Microorganism | Original | 1 wash | 3 washes | 5 washes | 10 washes | 12 washes |
| --- | --- | --- | --- | --- | --- | --- |
| Staphylococcus aureus | 2 | 2 | 1 | 1 | 1 | 1 |
| Pseudomonas aeruginosa | 0 | 0 | 0 | 0 | s | s |
| Escherichia coli | 0 | 0 | s | s | s | m |
| Klebsiella pneumoniae | 1 | 1 | 0 | 0 | 0 | s |
| Candida albicans | 4 | 4 | 3 | 3 | 2 | 2 |

This test shows very clearly the antimicrobial performance difference between the formulation according to the invention and a commercially available product. This aspect must be added to the huge advantages which the product has in application by reason of its composition alone.

Results to Example 8 (pad-mangle application to polyester):

| Microorganism | Original | 5 washes | 10 washes | 12 washes |
| --- | --- | --- | --- | --- |
| Staphylococcus aureus | 6 | 0 | 0 | 0 |
| Pseudomonas aeruginosa | 0 | 0 | 0 | 0 |
| Escherichia coli | 0 | 0 | 0 | 0 |
| Klebsiella pneumoniae | 5 | 0 | 0 | 0 |
| Candida albicans | 10 | 1 | 0 | 0 |

Results to Example 9 (pad-mangle application to wool):

| Microorganism | Original | 5 washes | 10 washes | 12 washes |
| --- | --- | --- | --- | --- |
| Staphylococcus aureus | 2 | 0 | 0 | 0 |
| Pseudomonas aeruginosa | 0 | 0 | 0 | 0 |
| Escherichia coli | 0 | 0 | 0 | 0 |

-continued

| Microorganism | Original | 5 washes | 10 washes | 12 washes |
|---|---|---|---|---|
| Klebsiella pneumoniae | 0 | 0 | 0 | 0 |
| Candida albicans | 5 | 0 | 0 | 0 |

Results to Example 10 (exhaustion onto cotton):

| Microorganism | Original | 5 washes | 10 washes | 12 washes |
|---|---|---|---|---|
| Staphylococcus aureus | 5 | 5 | 3 | 2 |
| Pseudomonas aeruginosa | 0 | 0 | 0 | 0 |
| Escherichia coli | 0 | 0 | 0 | 0 |
| Klebsiella pneumoniae | 2 | 0 | 0 | 0 |
| Candida albicans | 8 | 6 | 3 | 2 |

Results to Example 10 (exhaustion onto nylon):

| Microorganism | Original | 5 washes | 10 washes | 12 washes |
|---|---|---|---|---|
| Staphylococcus aureus | 2 | 0 | 0 | 0 |
| Pseudomonas aeruginosa | 0 | 0 | 0 | 0 |
| Escherichia coli | 0 | 0 | 0 | 0 |
| Klebsiella pneumoniae | 0 | 0 | 0 | 0 |
| Candida albicans | 3 | 0 | 0 | 0 |

Results to Example 10 (exhaustion onto polyester):

| Microorganism | Original | 5 washes | 10 washes | 12 washes |
|---|---|---|---|---|
| Staphylococcus aureus | 0 | 0 | 0 | 0 |
| Pseudomonas aeruginosa | 0 | 0 | 0 | 0 |
| Escherichia coli | 0 | 0 | 0 | 0 |
| Klebsiella pneumoniae | 0 | 0 | 0 | 0 |
| Candida albicans | 1 | 0 | 0 | 0 |

Results to Example 10 (exhaustion onto wool):

| Microorganism | Original | 5 washes | 10 washes | 12 washes |
|---|---|---|---|---|
| Staphylococcus aureus | 0 | 0 | 0 | 0 |
| Pseudomonas aeruginosa | 0 | 0 | 0 | 0 |
| Escherichia coli | 0 | 0 | 0 | 0 |
| Klebsiella pneumoniae | 0 | 0 | 0 | 0 |
| Candida albicans | 2 | 0 | 0 | 0 |

Results to Example 11 (application together with Nuva CSF):

|  | Cotton | Nylon |
|---|---|---|
| Staphylococcus aureus | 4 | 0 |
| Escherichia coli | S | S |
| Pseudomonas aeruginosa | M | M |
| Klebsiella pneumoniae | 1 | 0 |
| Candida albicans | 0 | M |

Results to the further Examples 12 to 16:

| Substrate | Example 12 Cotton | Example 12 Nylon | Example 13 Cotton | Example 13 Nylon |
|---|---|---|---|---|
| Textile chemical | Sandolub NV | Sandolub NV | Sandoperm MEW | Sandoperm MEW |
| Staphylococcus aureus | 4 | 4 | 5 | 5 |
| Pseudomonas aeruginosa | 0 | 0 | 0 | 0 |
| Escherichia coli | 2 | 2 | 4 | 3 |
| Klebsiella pneumoniae | 3 | 3 | 4 | 3 |
| Candida albicans | 6 | 6 | 6 | 6 |

| Substrate | Example 14 Cotton | Example 14 Nylon | Example 15 Cotton | Example 15 Nylon |
|---|---|---|---|---|
| Textile chemical | Pekoflam OP | Pekoflam OP | Appretan EM | Appretan EM |
| Staphylococcus aureus | 4 | 4 | 6 | 2 |
| Pseudomonas aeruginosa | 0 | 0 | 0 | 0 |
| Escherichia coli | 5 | 5 | 3 | 2 |
| Klebsiella pneumoniae | 4 | 4 | 3 | 3 |
| Candida albicans | 6 | 7 | 6 | 5 | with filter paper, Example 16

| Staphylococcus aureus | Pseudomonas Aeruginosa | Escherichia coli | Klebsiella Pneumoniae |
|---|---|---|---|
| 2 | 0 | 0 | 0 |

What is claimed is:

1. A process for preparing an antimicrobial formulation by reacting a compound of the formula 1

$$(R^1O)_3Si-(CH_2)_3-X \qquad (1)$$

with a compound of the formula 2

$$(H_3C)NR^2R^3 \qquad (2)$$

where $R^1$ is $C_1$–$C_4$-alkyl $R^2$ is $C_8$–$C_{20}$-alkyl $R^3$ is methyl or $C_8$–$C_{20}$-alkyl x is Cl or Br, excluding iodides, in a molar ratio of (1):(2)=1:0.9 to 1:1.4, which comprises conducting said reaction in a solvent conforming to the formula 3

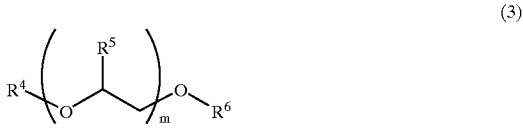

(3)

where $R^4$ is $C_1$–$C_4$-alkyl $R^5$ is H or methyl $R^6$ is H or methyl m is 2, 3, 4 or 5, subject to the proviso that when m is 2 $R^4$ and $R^6$ are not both methyl, and not removing this solvent after said reaction, or adding this solvent after said reaction.

2. The process of claim 1, wherein $R^1$ is methyl.

3. The process of claim 1, wherein $R^2$ is $C_{10}$–$C_{18}$-alkyl.

4. The process of claim 1, wherein $R^3$ is $C_8$–$C_{16}$-alkyl.

5. The process of claim 1, wherein $R^2$ is $C_{14}$-alkyl and $R^3$ is methyl.

6. The process of claim 1, wherein $R^4$ is methyl.

7. The process of claim 1, wherein $R^5$ is hydrogen.

8. The process of claim 1, wherein $R^6$ is H.

9. The process of claim 1, wherein m is 3 or 4.

10. An antimicrobial formulation obtainable as claimed in claim 1.

11. A method for the antimicrobial finishing of surfaces, which comprises using a formulation as claimed in claim 10.

* * * * *